United States Patent
Reinschke

(10) Patent No.: US 8,452,377 B2
(45) Date of Patent: May 28, 2013

(54) COIL ASSEMBLY FOR GUIDING A MAGNETIC OBJECT IN A WORKSPACE

(75) Inventor: Johannes Reinschke, Nürnberg (DE)

(73) Assignee: Siemens Aktiengesellshaft, Munich (DE)

( * ) Notice: Subject to any disclaimer, the term of this patent is extended or adjusted under 35 U.S.C. 154(b) by 0 days.

(21) Appl. No.: 13/254,132

(22) PCT Filed: Feb. 12, 2010

(86) PCT No.: PCT/EP2010/051771
§ 371 (c)(1),
(2), (4) Date: Aug. 31, 2011

(87) PCT Pub. No.: WO2010/105882
PCT Pub. Date: Sep. 23, 2010

(65) Prior Publication Data
US 2011/0316656 A1 Dec. 29, 2011

(30) Foreign Application Priority Data
Mar. 16, 2009 (DE) .......................... 10 2009 013 352

(51) Int. Cl.
*H01F 5/00* (2006.01)
*A61B 5/05* (2006.01)
*A61B 6/00* (2006.01)
*A61M 25/00* (2006.01)

(52) U.S. Cl.
USPC ........................... 600/424; 600/434; 335/299

(58) Field of Classification Search
USPC .... 335/229; 600/424, 417, 423, 434; 606/130
See application file for complete search history.

(56) References Cited

U.S. PATENT DOCUMENTS

| 5,558,091 | A | * | 9/1996 | Acker et al. ................... | 600/424 |
| 6,475,223 | B1 | * | 11/2002 | Werp et al. ..................... | 606/108 |
| 7,173,507 | B2 | * | 2/2007 | Ries .............................. | 335/299 |
| 7,663,458 | B2 | * | 2/2010 | Reinschke et al. ............. | 335/299 |
| 2004/0249262 | A1 | * | 12/2004 | Werp et al. ..................... | 600/411 |
| 2005/0256398 | A1 | * | 11/2005 | Hastings et al. ............... | 600/423 |
| 2007/0221233 | A1 | | 9/2007 | Kawano et al. | |
| 2007/0232899 | A1 | * | 10/2007 | Bill et al. ....................... | 600/424 |
| 2008/0262292 | A1 | * | 10/2008 | Abraham-Fuchs et al. .. | 600/101 |
| 2008/0272873 | A1 | * | 11/2008 | Reinschke et al. ............ | 335/299 |
| 2010/0022835 | A1 | | 1/2010 | Kimura et al. | |
| 2011/0054254 | A1 | | 3/2011 | Reinschke | |

FOREIGN PATENT DOCUMENTS

WO WO 2007/110278 A1 10/2007
WO WO 2009/016207 A1 2/2009

OTHER PUBLICATIONS

"Control Strategy of Active Actuation System of Wireless Capsule Endoscope," Hu et al., Proc. of the 2007 IEEE Int. Conf. on Integration Technology (2007) pp. 1-6.

* cited by examiner

*Primary Examiner* — Alexander Talpalatski
(74) *Attorney, Agent, or Firm* — Schiff Hardin LLP

(57) ABSTRACT

A coil assembly for guiding a magnetic object, such as an endoscopy capsule, in a workspace, wherein the magnetic object exhibits a magnetic dipole, includes different versions of coil assemblies having a number of individual coils and corresponding activation units for feeding current to the respective coils. The coil arrangement can have exactly eleven individual coils and eight power amplifiers, nine individual coils and seven power amplifiers, eight individual coils with six or seven power amplifiers, six individual coils with five power amplifiers, and five individual coils with five power amplifiers.

33 Claims, 6 Drawing Sheets

COIL ASSEMBLY FOR GUIDING A MAGNETIC OBJECT IN A WORKSPACE

BACKGROUND OF THE INVENTION

1. Field of the Invention

The invention concerns a coil arrangement for contact-less guidance of a magnetic object (in particular an endoscopy capsule) in a workspace.

2. Description of the Prior Art

The use of endoscopes and catheters has an ever increasing application in medicine for the diagnosis or treatment of the inside of a patient. The instruments are introduced into the body via bodily orifices or incisions and, directed from the outside, can be displaced in a longitudinal direction, for which a mechanical connection to the instrument is necessary. However, in the case of forward movement of the instrument in the body, difficulties in the navigation occur regularly at curves or branches, such that the operator must direct the instrument in the desired direction (possibly via repeated attempts) and a supporting force of the tissue on the instrument is required for the further navigation. This is associated with high time expenditure by the operator and pain for the patient. In the worst case it is not precluded that the guidance in the planned direction cannot be achieved at all, or that the risk of tissue perforation arises. Furthermore, in the case of endoscopy it can be of interest to rotate the endoscopy head (equipped with a camera) in specific directions, for example in order to be able to completely view the mucous membrane in a segment of the gastrointestinal tract. This is only conditionally possible with modern catheter endoscopes because the catheter tip has only limited mobility. Moreover, typical catheter endoscopes have the disadvantage that remotely situated internal organs can only be reached with difficulty, or cannot be reached at all.

The passive endoscopy capsule moved by the natural peristalsis of the gastrointestinal tract does not have the cited disadvantages of the catheter endoscope, but it cannot be navigated, meaning that the targeted viewing of specific points inside the gastrointestinal tract is not possible. Therefore, magnetic navigation or guidance systems have been proposed that enable a catheter-free wireless guidance of endoscopy capsules that embody a magnetic dipole moment. A catheter-free or wireless guidance is also designated as "contact-free" in the following.

DE 103 40 925 B3 and WO 2006/092421 A1 respectively describe a magnetic coil arrangement consisting of 14 individual coils for navigation of an endoscopy capsule, a video capsule or another probe. The capsule is hereby equipped with a magnetic element, for example a permanent or ferromagnet. The magnetic coil arrangement generates magnetic field components $B_x$, $B_y$, $B_z$ along the axes x, y, z of a Cartesian coordinate system, as well as magnetic gradient fields that enable a contact-less guidance of the endoscopy capsule.

In such system, use is made of the fact that the magnetic element (i.e. a body with a magnetic dipole moment m) will attempt to align itself parallel to the direction of the magnetic field B consisting of the magnetic field components $B_x$, $B_y$, $B_z$ in the direction of the axes of the Cartesian coordinate system. Since the magnetic element is firmly connected with the endoscopy capsule, the orientation of the capsule can thus be affected. A force $F=G \cdot m$ (initiated by the magnetic gradient fields $\partial B_x/\partial x$ etc.) additionally acts on the magnetic dipole moment m with a gradient matrix G comprising the gradient fields according to $$F = G \cdot m = \begin{pmatrix} \partial B_x/\partial x & \partial B_x/\partial y & \partial B_x/\partial z \\ \partial B_y/\partial x & \partial B_y/\partial y & \partial B_y/\partial z \\ \partial B_z/\partial x & \partial B_z/\partial y & \partial B_z/\partial z \end{pmatrix} \cdot m$$

Analogously to the magnetic field B, the force F and the magnetic moment m are thereby three-dimensional vectors with corresponding x-, y- and z-components. The 3×3 gradient matrix G is symmetrical and spur-free due to the Maxwell equations curl H=0 and div B=0, as well as due to $B=\mu_0 \cdot H$, meaning that—with $\partial B_x/\partial y$ (=$\partial B_y/\partial x$), $\partial B_x/\partial z$ (=$\partial B_z/\partial x$), $\partial B_y/\partial z$ (=$\partial B_z/\partial y$) and two of the three diagonal elements (for example $\partial B_x/\partial x$ and $\partial B_y/\partial y$)—it contains five independent gradient fields.

The magnetic field B and the gradient fields can be adjusted arbitrarily via a targeted activation of the individual coils of the magnetic coil arrangement. It is therefore possible to rotate the magnetic object and thus to align it arbitrarily in a work space within the magnetic coil arrangement. Moreover, it is possible to exert a force F on the magnetic object in order to displace it translationally in addition to the rotation. For this eight quasi-static magnetic degrees of freedom are realized, namely the magnetic field components $B_x$, $B_y$, $B_z$ as well as two of the three entries of the diagonal elements (for example $\partial B_x/\partial x$ and $\partial B_y/\partial y$) and three of the secondary diagonal elements (for example $\partial B_x/\partial y$, $\partial B_z/\partial x$, $\partial B_z/\partial y$) of the gradient matrix G.

The systems described in DE 103 40 925 B3 and WO 2006/092421 A1 have the disadvantage that they are relatively cost-intensive in their manufacture and installation due to the 14 individually activated coils that are required there due to the high number of coils and activation units (in the form of power amplifiers).

SUMMARY OF THE INVENTION

It is therefore an object of the invention to provide a more cost-effective magnetic guidance system of the type having a coil arrangement and multiple activation units associated with the coils.

The coil arrangement according to the invention serves to guide a magnetic object with a magnetic dipole moment in a work space for which a Cartesian coordinate system is provided, with three axes, namely a horizontal first axis, a horizontal second axis and a vertical third axis. The coil arrangement has a number of individual coils for the generation of components of a magnetic field and of gradient fields, wherein the gradient fields are described by the gradient matrix G described in the preceding. A number of activation units is also provided that can be realized as corresponding power amplifiers.

In order to achieve a movement of a magnetic object in every spatial direction with a low number of individual coils according to a first embodiment of the invention, the following embodiment and arrangement of individual coils is used:

The number of individual coils includes a number of first individual coils, wherein the work space (as viewed from the direction of the longitudinal axis of the respective first individual coil) lies within the circumference of the respective first individual coil. Here and in the following the longitudinal axis of an individual coil designates the axis around which the windings of the coil extend. The windings thereby form the circumference of the coil. The width of an individual coil in the following designates the width of the windings in the direction of the longitudinal axis.

According to the invention, at least one first coil pair composed of two first individual coils is respectively associated with one or more axes of the Cartesian coordinate system, which individual coils are arranged along the respective axis on opposite sides of the work space in essentially parallel planes. In order to keep the number of coils as low as possible, instead of a first coil pair a single first individual coil or no first individual coil is associated with one or more of the axes of the Cartesian coordinate system, wherein the case "no first individual coil" means that neither a coil pair composed of first individual coils nor a first individual coil is provided along the axis. If a first individual coil is used instead of the coil pair, the work space is at least partially surrounded by the circumference of a respective, single first individual coil, meaning that the width of the circumference at least partially covers the work space.

A number of second individual coils is also provided in addition to the first individual coils, wherein the work space in the direction of the longitudinal axis of a respective second individual coil is situated outside of the circumference of the respective second individual coil. A second coil pair composed of two second individual coils is respectively associated with one or more of the axes of the Cartesian coordinate system, which second individual coils are essentially arranged in a common plane on opposite sides of the work space along the respective axis. Here and in the following, a common plane means a plane that extends through the circumference of the second coils of the respective coil pair. A wing-like arrangement of the corresponding second individual coils of a second coil pair thus exists in the environment of the work space.

The above embodiment of the coil arrangement according to the invention has the advantage that the number of individual coils that are used is reduced in that at least one coil pair composed of two first individual coils is replaced with a single first individual coil. In a particularly preferred variant, the number of activation units that is used is also further reduced in that at least two individual coils can be activated by a common activation unit.

A specific design of the first embodiment of the invention has precisely eleven individual coils. Two first coil pairs are provided, wherein one of the first coil pairs is associated with the first axis and the other of the first coil pairs is associated with the third axis. In contrast, a single first individual coil is associated with the second axis. A second coil pair is also provided which is associated with the first axis and is arranged in a plane which is spanned by the first and third axes. Moreover, two second coil pairs are provided that are associated with the third axis and which are arranged essentially perpendicular to one another in planes, wherein one of the planes is spanned by the first and third axes and the other of the planes is spanned by the second and third axes. In this way a magnetic object on which forces are exerted with the coil arrangement can be aligned arbitrarily in space with only eleven coils, and arbitrary forces can be exerted on the magnetic object.

In an alternative variant that likewise enables an arbitrary alignment and force exertion on the magnetic object, analogously to the embodiment just described, has the same first coil pairs and the same first individual coil. A second coil pair is likewise also provided which is associated with the first axis and is arranged in a plane which is spanned by the first and third axes. In contrast to the preceding embodiment, an additional second coil pair is provided which is associated with the first axis and is arranged in a plane which is spanned by the first and second axes.

In a preferred variant of the two specific exemplary embodiments described above, a minimal number of eight activation units for activation of the coils. In operation of the coil arrangement all first individual coils are thereby activated by separate activation units, and the second coil pairs are respectively activated by a common activation unit.

A second embodiment of the invention serves to align a magnetic object arbitrarily in space and to exert magnetic fields on the magnetic object only in the plane that is spanned by the direction of the magnetic dipole moment of the magnetic object and the vertical axis. In the field of capsule endoscopy this variant is in particular used for a stomach screening as it is described in the publication WO 2007/077922 A1, for example. In the stomach of the patient the endoscopy capsule thereby moves in water that the patient has consumed beforehand.

In one design of the second embodiment, the coil arrangement has precisely nine individual coils. Two first coil pairs are provided, wherein one of the first coil pairs is associated with the first axis and the other of the first coil pairs is associated with the third axis. A single first individual coil is also provided which is associated with the second axis. Moreover, the coil arrangement has two second coil pairs that are associated with the third axis and that are arranged in planes essentially perpendicular to one another, wherein one of the planes is spanned by the first and third axes and the other of the planes is spanned by the second and third axes.

In an alternative variant of the above embodiment with nine coils, the same first coil pairs, the same single first individual coil and the same second coil pair associated with the third axis and situated in the plane of the first and third axes are provided. However, in contrast to the preceding embodiment a second coil pair is now provided which is associated with the first axis and arranged in a plane which is spanned by the first and second axes.

In a preferred variant of the designs of the second embodiment that are described above, precisely seven activation units are used, wherein all first individual coils can be activated by separate activation units and the second coil pairs can respectively be activated by a common activation unit.

A third embodiment of the coil arrangement according to the invention serves to align a magnetic object arbitrarily in space and to exert magnetic fields on said magnetic object only in the direction of the longitudinal axis of said magnetic object. The magnetic dipole moment of the object is situated perpendicular to the longitudinal axis of the object. When used for capsule endoscopy, this embodiment serves to move an endoscopy capsule through the small intestine and/or large intestine of the patient to be examined in the manner of a tube navigation.

In one variant of this third embodiment, the coil arrangement comprises precisely eight individual coils. A first coil pair is provided that is associated with the third axis, as well as a second coil pair that is associated with the first axis and is arranged in a plane which is spanned by the first and third axes. Two additional second coil pairs are also provided that are associated with the third axis and that are arranged essentially perpendicular to one another in planes, wherein one of the planes is spanned by the first and third axes and the other of the planes is spanned by the second and third axes.

In a further variant of the third embodiment, the coil arrangement composed of eight individual coils has a first coil pair which is associated with the first axis; a second coil pair which is associated with the first axis and is arranged in a plane that is spanned by the first and third axes; and an additional second coil pair that is associated with the first axis and is arranged in a plane that is spanned by the first and second axes. Moreover, an additional second coil pair is also provided that is associated with the third axis and arranged in a plane that is spanned by the first and third axes.

In the variants of the third embodiment that were just described, exactly seven activation units can be provided, wherein all second individual coils can be activated by separate activation units and the two first individual coils of the first coil pair can be activated by a common activation unit. Alternatively, the number of activation units can be reduced to six, wherein in this case the second individual coils of the second coil pair—which is associated with the first axis and arranged in one plane which is spanned by the first and third axes—can be activated by a common activation unit. The two first individual coils of the first coil pair can also likewise be activated by a common activation unit. In this embodiment all remaining individual coils of the coil arrangement can be activated by separate activation units.

In a fourth embodiment of the coil arrangement according to the invention, it is possible to arbitrarily align the magnetic object in space and to exert magnetic forces only in the direction of the longitudinal axis of the magnetic object. The magnetic dipole moment of the magnetic element in the magnetic object is aligned along the longitudinal axis of the magnetic object, which leads to the limitation that—in contrast to the preceding embodiment—the magnetic object (for example in the form of a capsule) cannot be rotated around its longitudinal axis. This embodiment is advantageously used in the field of capsule endoscopy, and in fact in "tube navigation" of capsules through the small intestine or large intestine.

In a first variant of the fourth embodiment, only first coil pairs composed of first individual coils are provided, wherein the first individual coil of at least one first coil pair can be activated by a common activation unit.

In this variant the second coil pair arranged like wings can be omitted entirely, and the number of power amplifiers is reduced in that at least one first coil pair is activated by a common activation unit. In a preferred variant, six first individual coils are thereby provided, wherein a first coil pair composed of two first individual coils is associated with each axis. This variant advantageously has precisely five activation units, wherein the two first individual coils of a first coil pair can be activated with one common activation unit and the remaining first individual coils can be activated by separate activation units.

In a further variant of the fourth embodiment of the coil arrangement according to the invention first individual coils are again provided exclusively, wherein now—instead of a first coil pair—a respective, single first individual coil is associated with one or more of the axes of the Cartesian coordinate system, wherein the work space is at least partially surrounded by the circumference of a respective, single first individual coil. All first individual coils can be activated by separate activation units. In a preferred variant, the coil arrangement has precisely five first individual coils, meaning that two second coil pairs are provided and exactly one first coil pair is replaced with a single first individual coil.

In a preferred design of the embodiments of the coil arrangement according to the invention that are described above, the individual coils at least in part comprise ring coils and/or saddle coils. The individual coils can likewise at least in part be surface coils, in particular with a width in the longitudinal direction which is greater than the thickness of the coil, wherein the width is at least ten times the thickness. In particular, each variant of the embodiments of coils that are described in the German Patent Application with the number 10 2008 004 871.2-35 can be used in the arrangement according to the invention. The complete disclosure content of German Patent Application 10 2008 004 871.2-35 is incorporated.

As mentioned, the coil arrangement according to the invention is advantageously used in the field of magnetic capsule endoscopy. In a preferred variant, the coil arrangement includes a patient table on which the patient to be examined lies during operation of the coil arrangement, wherein the patient table is arranged such that the longitudinal axis of a patient on the patient table extends essentially in the direction of the second axis of the Cartesian coordinate system.

DESCRIPTION OF THE PREFERRED EMBODIMENTS

Figure 1:
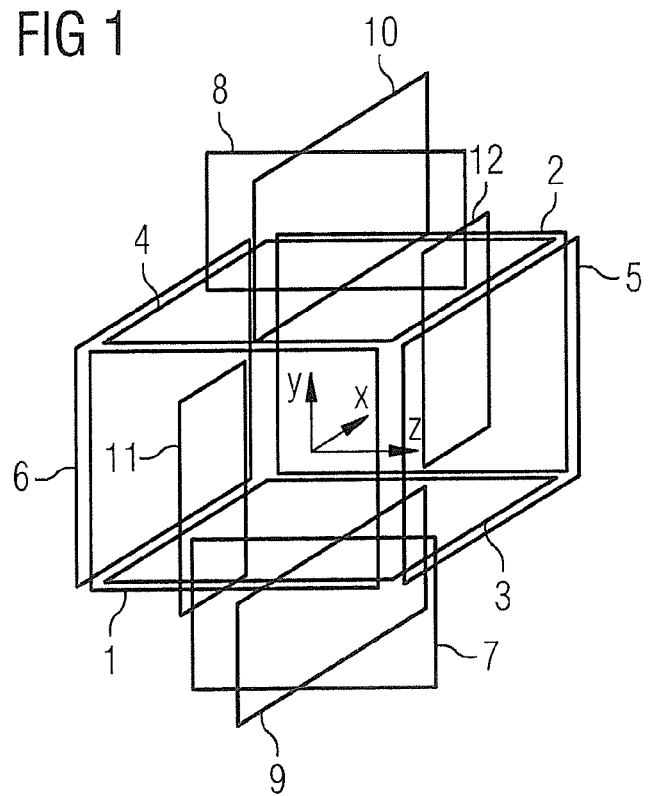
FIG. 1 schematically illustrates a twelve coil system with eight power amplifiers, as disclosed in German Patent Application 10 2008 004 871.2-35.

Before the individual embodiments are described, the relationship between the magnetic dipole moment of an object guided with the coil arrangement according to the invention and the current flow or the correspondingly generated magnetic field of the coil system according to the invention will be explained. An endoscopy capsule that exhibits or embodies a magnetic element (for example a permanent magnet) and that is positioned inside a patient (not shown)—for example in that the patient swallows the capsule—is advantageously used as a magnetic object. Such a capsule typically has a camera to acquire images of internal organs of the patient as well as a corresponding transmission module with which the acquired images are sent to an extracorporeal processing unit having a corresponding receiver. In the following the magnetic dipole moment is designated with m; it represents a three-dimensional vector. The dipole moment is generated (for example with the use of a permanent magnet) and in the capsule can be aligned in the direction of the longitudinal axis of said capsule or, respectively, can also be aligned perpendicular to the longitudinal axis of the capsule if necessary. The permanent magnet is firmly connected with the endoscopy capsule so that forces and torques on the permanent magnet that are generated by the coil arrangement according to the invention are transferred directly to the endoscopy capsule.

In general it is assumed that in the coil system n coils are provided in which the currents $I_1$ through $I_n$ flow. In vector notation, the magnetic moment m and the coil current vector I are as follows:

$$m = \begin{pmatrix} m_x \\ m_y \\ m_z \end{pmatrix}$$

$$I = \begin{pmatrix} I_1 \\ \vdots \\ I_n \end{pmatrix}$$

wherein $m_x$, $m_y$ or, respectively, $m_z$ represent the components of the magnetic dipole moment in the direction of the x- or, respectively, y- or, respectively, z-axis of the Cartesian coordinate system associated with the coil system.

Via the coil currents, a magnetic field is generated that exerts a torque on the endoscopy capsule so that the endoscopy capsule aligns in the direction of the field lines of the magnetic field. A magnetic force on the endoscopy capsule also results due to the gradients of the magnetic field generated by means of the coil system. This force is designated as F in the following and reads as follows in vector notation:

$$F = \begin{pmatrix} F_x \\ F_y \\ F_z \end{pmatrix}$$

wherein $F_x$, $F_y$ and $F_z$ represent the corresponding components of the force in the x-direction, y-direction and z-direction, respectively.

In matrix notation the following connection results between the magnetic field B and the force F generated at location r by the coil system and the coil current vector I:

$$\begin{pmatrix} B \\ F \end{pmatrix} = \begin{pmatrix} U_1 & 0 \\ 0 & U_2 \end{pmatrix} \begin{pmatrix} V_1 \\ V_2 \end{pmatrix} I$$

The following applies:

$$U_1 = \begin{pmatrix} 1 & 0 & 0 \\ 0 & 1 & 0 \\ 0 & 0 & 1 \end{pmatrix}$$

$$F = \begin{pmatrix} F_x \\ F_y \\ F_z \end{pmatrix}, \quad V_2 \cdot I = \begin{pmatrix} \partial B_x / \partial x \\ \partial B_y / \partial x \\ \partial B_z / \partial x \\ \partial B_z / \partial y \\ \partial B_y / \partial y \end{pmatrix}$$

wherein $V_1$ and $V_2$ are matrices that are predetermined by the location r and the concrete embodiment of the coil system. It is recognized that the magnetic force F depends on only five gradient fields $\partial B_x/\partial x$, $\partial B_y/\partial x$, $\partial B_z/\partial z$, $\partial B_z/\partial y$ and $\partial B_y/\partial y$, which results from the fact (explained in the preceding) that the gradient matrix is symmetrical and spur-free due to the Maxwell equations.

Based on the Equation $F = G \cdot m$, the following values result for the matrix $U_2$.

$$U_2 = \begin{pmatrix} m_x & m_y & m_z & 0 & 0 \\ 0 & m_x & 0 & m_z & m_y \\ -m_z & 0 & m_x & m_y & -m_z \end{pmatrix}$$

$$ColumnNr. \rightarrow \quad 1 \quad 2 \quad 3 \quad 4 \quad 5$$

Given the movement of an endoscopy capsule, different scenarios of predeterminable movement directions and alignments of the dipole moment are thereby conceivable that are relevant for different medical applications. Different configurations of coil systems and corresponding power amplifiers to activate the coil systems result from these. In specific scenarios, based on predetermined boundary conditions pairs of coils can thereby be activated with the same power amplifiers and specific coil pairs can be omitted or, respectively, replaced with a single coil. In the following embodiments are described with which minimal coil system configurations—i.e. configurations with an optimally low number of coils and power amplifiers—can be achieved depending on different requirements.

Figure 2:
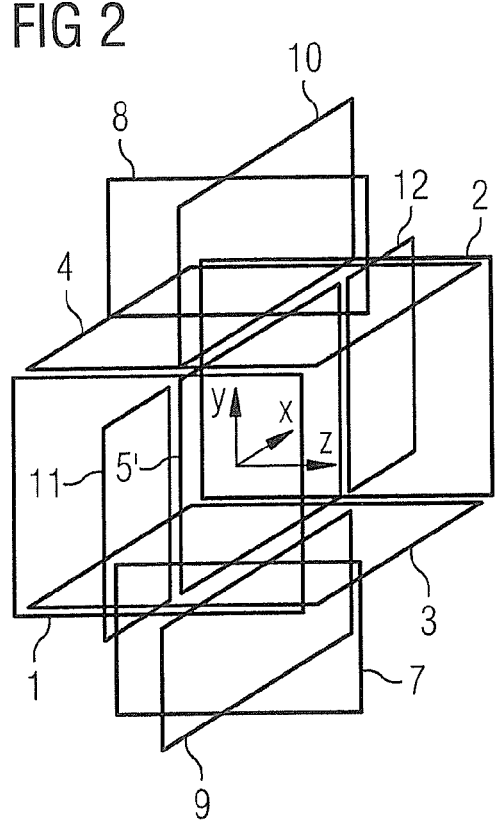
FIG. 2 schematically illustrates an eleven coil system with eight power amplifiers according to a first embodiment of the present invention.
Figure 3:
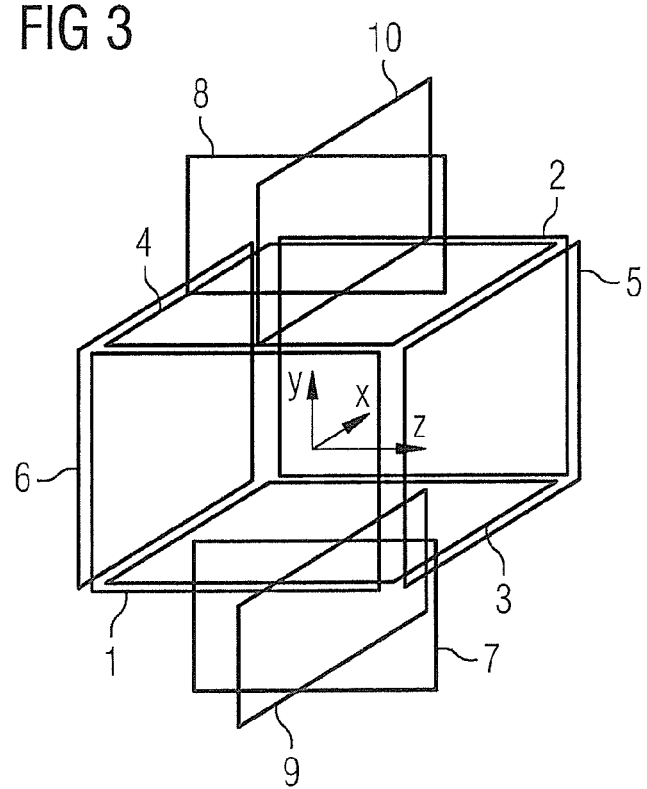
FIGS. 3 and 4 schematically illustrate a ten coil system with seven power amplifiers, as described in German Patent Application 10 2008 004 871.2-35.

Using FIG. 1 through FIG. 3, coil system configurations are initially explained with which it is possible to arbitrarily align an endoscopy capsule in space and to exert a magnetic field on the capsule in arbitrary spatial directions. These navigation requirements are designated as a case. As presented above, the magnetic force F linearly depends on the magnetic dipole moment m of the capsule. Therefore, for the following case (A) as well as all further cases (B) through (D) it is sufficient to analyze the following scenarios:

(X) the dipole moment is aligned in the x-direction,
(Y) the dipole moment is aligned in the y-direction,
(Z) the dipole moment is aligned in the z-direction.

According to the case (A.X) in which the dipole moment has only the x-component $m_x$, only the columns with the numbers 1, 2 and 3 of the above matrix $U_2$ which are combined with the field gradients $\partial B_x/\partial x$, $\partial B_y/\partial y$ and $\partial B_z/\partial x$ are relevant. For the case (A.Y), due to the dipole moment $m_y$, only the columns with the numbers 2, 4 and 5 of the above matrix $U_2$ are relevant. For the case (A.Z) in which only a dipole moment with the component $m_z$ is present, only the columns with the numbers 3, 4 and 5 of $U_2$ play a role. From the combination of all of the above cases it results that all five field gradients in connection with the three magnetic basic field components are required for the case (A), meaning that at least eight power amplifiers are required to activate the coils of the coil system.

In a schematic presentation, FIG. 1 shows a corresponding 12-coil system with eight power amplifiers the design of which is ascribed to the German Patent Application Nr. 10 2008 004 871.2-35. All embodiments of usable coils that are shown in this German Patent Application can also be used in the variants according to the invention of the coil systems described in the following. The coil system shown in FIG. 1 comprises the twelve individual coils 1 through 12, wherein (analogously to the aforementioned earlier German Patent Application) the first through fourth coil 1 through 4 can be fashioned as identically shaped saddle coils that surround a work space that is arranged in the region of the shown Cartesian coordinate system with the horizontal x-axis and z-axis, and the vertical y-axis.

Given the use of the coil system for capsule endoscopy, in FIG. 1 (and also in the embodiments of all other Figures) a body section of the patient is surrounded by the coils 1 through 4 during the implementation of the endoscopy examination, meaning that the longitudinal axis of the patient runs parallel to the z-axis. The body of the patient thus extends through the inside of the additional coils 5 and 6 which (analogously to the aforementioned earlier German Patent Application) can be designed as annular coils. The movement of the corresponding magnetic object or, respectively, of the endoscopy capsule thereby takes place in the work space, meaning that the work space is situated inside the patient body. Instead of the use of saddle coils 1 through 4 and annular coils 5 and 6, surface coils can also be used which—in contrast to saddle coils—are fashioned flat and advantageously have a rectangular cross section. The surface coils are thereby advantageously fashioned as broad surface coils whose winding package is wider than it is high, meaning that the width along the longitudinal axis of the coil is significantly greater than the thickness or, respectively, the winding height of the coil.

As results from FIG. 1, the coils 1 through 6 surround the work space; its origin is reflected by the origin of the shown coordinate system. The work space is thereby arranged centered in the volume formed by the coils 1 through 6, and it represents a cuboid whose opposite sides have approximately half the clearance as the corresponding opposite coils. The coils 1 through 6 thus represent first individual coils, in which the work space (as viewed from the direction of the longitudinal axis of a respective individual coil) lies within the circumference of the respective coil. Corresponding opposite coils 1 and 2 and opposite coils 3 and 4 and opposite coils 5 and 6 represent first coil pairs, each of which has a corresponding axis of the Cartesian coordinate system associated therewith, with the individual coils of the coil pair being arranged on opposite sides of the work space in essentially parallel planes. The coil pair composed of coils 1 and 2 thereby serves to generate the magnetic field component $B_x$ of the generated magnetic field B, wherein given a separate activation of the two coils with a respective power amplifier the gradient field $\partial B_x/\partial x$ can also be generated. The coils 3 and 4 serve to adjust the magnetic field component $B_y$, wherein the gradient field $\partial B_y/\partial y$ can also be generated in the event that the two coils are activated by separate power amplifiers. The coils 5 and 6 serve to generate the magnetic field component $B_z$, wherein the gradient field $\partial B_z/\partial z$ can also be generated insofar as the two coils of the coil pair are activated by separate power amplifiers. Insofar as corresponding coils 1 through 6 are referenced in all additional embodiments, these coils are arranged analogously to as in FIG. 1 and also have the same function of the generation of a magnetic field component or, respectively, of a gradient field.

In order to also generate the secondary diagonal elements of the gradient matrix G described above, in the example of FIG. 1 coils 8 through 12 are also provided that represent second individual coils in the sense of the Claims. The coils 7 and 8 thereby form a coil pair whose two coils are arranged offset from the work space along the y-axis in the y-z plane. The coils 9 and 10 likewise form a coil pair that is arranged offset by the work space along the y-axis but is arranged rotated in the x-y plane relative to the coil pair made up of coils 7 and 8. A coil pair composed of coils 11 and 12 is also provided, wherein the coils are arranged on opposite sides of the work space, offset relative to one another along the x-axis in the x-y plane. The coils collectively represent second individual coils for which the work space (as viewed from the direction of the longitudinal axis of a respective coil of the individual coils 7 through 12) lies outside of the circumference of the respective coil.

To generate the corresponding gradient fields according to the secondary diagonal elements of the gradient matrix G, the individual coils 7, 8, and 9, 10, and 11, 12 of the respective coil pairs are activated with a common power amplifier. The coil pair composed of individual coils 7 and 8 serves to generate the gradient field $\partial B_y/\partial x$ (=$\partial B_x/\partial y$); the coil pair composed of individual coils 9 and 10 generates the gradient field $\partial B_z/\partial y$ (=$\partial B_y/\partial z$); and the coil pair composed of individual coils 11 and 12 serves to generate the gradient field $\partial B_x/\partial z$ (=$\partial B_z/\partial x$). To generate the gradient field $\partial B_x/\partial y$, the coil pair 7 and 8 can possibly also be arranged as rendered in FIG. 7, in which the two coils 7 and 8 are arranged along the x-axis in the x-y plane. Insofar as that the coils 7 through 12 are referenced here and in the following embodiments, the same association of the corresponding coil numbers with the generation of the gradient fields that is described above exists. In the normal case, the individual coils are thereby also arranged in the same geometric attitude as in FIG. 1 relative to the coordinate system. Only for the coils 7 and 8 do two alternative arrangements exist for the generation of the gradient field $\partial B_x/\partial y$.

As mentioned, eight power amplifiers are required to generate the three magnetic field components $B_x$, $B_y$ and $B_z$ as well as five gradient fields in order to move or align a magnetic object arbitrarily according to the above case (A). In a first variant, corresponding power amplifiers with the numbers 1 through 8 are thereby associated with the coils 1 through 12 as follows:

Power amplifier 1: Coil 1
Power amplifier 2: Coil 2
Power amplifier 3: Coil 3
Power amplifier 4: Coil 4
Power amplifier 5: Coils 5 and 6
Power amplifier 6: Coils 9 and 10
Power amplifier 7: Coils 7 and 8
Power amplifier 8: Coils 11 and 12

In a further variant, the association between power amplifiers and coils can analogously be designed as follows:

Power amplifier 1: Coils 1 and 2
Power amplifier 2: Coil 3
Power amplifier 4: Coil 6
Power amplifier 5: Coil 5
Power amplifier 6: Coils 9 and 10
Power amplifier 7: Coils 7 and 8
Power amplifier 8: Coils 11 and 12

Analogously, the possibility also exists to operate the coils 3 and 4 from the set of coils 1 through 6 with a common power amplifier, and to operate the remainder of these coils with separate power amplifiers, wherein the coils 7 through 12 are activated by power amplifiers in the same manner as described above.

FIG. 2 shows a variant of the coil system of FIG. 1, wherein this coil system represents a first embodiment of a coil arrangement according to the invention. It was thereby recognized that that coil pair made up of first individual coils which is operated with a common power amplifier according to the variant of the embodiment of FIG. 1 can be replaced with a single coil. In the embodiment of FIG. 2, instead of the coil pair made up of coils 5 and 6 a single individual coil 5' is consequently used which is arranged centrally between the two (now omitted) coils 5 and 6. The individual coil 5' is a wide surface coil having a winding thickness that is significantly less than its width in the z-direction. According to the coil arrangement according to FIG. 2, the number of coils that are used can thus be reduced from 12 to 11, so the costs for the coil system are reduced. The association of the individual power amplifiers 1 through 8 with the corresponding coils of the coil system of FIG. 2 is as follows:

Power amplifier 1: Coil 1
Power amplifier 2: Coil 2
Power amplifier 3: Coil 3
Power amplifier 4: Coil 4
Power amplifier 5: Coil 5'
Power amplifier 6: Coils 9 and 10
Power amplifier 7: Coils 7 and 8
Power amplifier 8: Coils 11 and 12

In the following, using FIG. 3 through FIG. 5 embodiments are described which are used in combination with a magnetic object which should be capable of being arbitrarily aligned in space, wherein magnetic forces should only be generated in the plane that is spanned by the magnetic dipole moment of the magnetic object and the vertical axis (i.e. the y-axis of the coil system). For example, in the field of capsule endoscopy this corresponds to the case that the capsule moves in water in the stomach of the patient, so the patient has consumed a larger quantity of water beforehand in the case of this examination. The buoyancy acting on the capsule in water thereby has the effect that the capsule swims on the water's surface with little or no magnetic force effect. This application case is designated as case (B) in the following. For the case (B.X) in which the dipole moment has only the component $m_x$, the force must lie in the x-y plane. This means that no force component $F_z$ must be generated and only the columns 1 and 2 of the matrix $U_2$ are combined with the field gradients $\partial B_x/\partial x$ and $\partial B_{xy}/\partial x$. For the case (B.Y) in which the dipole moment is aligned in the y-direction, the force must be aligned in the y-direction. This means that only the column 5 of the matrix $U_2$ is relevant to the generation of the force. For the case (B.Z) in which the dipole moment of the capsule is aligned in the z-direction, the force must lie in the y-z plane. In this case no force component $F_x$ is generated and only the columns with the numbers 4 and 5 of the matrix $U_2$ are relevant to the force generation. In summary, only entries in the columns 1, 2, 4 and 5 are relevant to the case (B), which means that only the field gradients $\partial B_x/\partial x$, $\partial B_y/\partial x$, $\partial B_z/\partial y$ and $\partial B_y/\partial y$—but not $\partial B_z/\partial x$—are required. In connection with the three basic magnetic field components, seven power amplifiers are thus sufficient to activate the coil arrangement.

Figure 4:
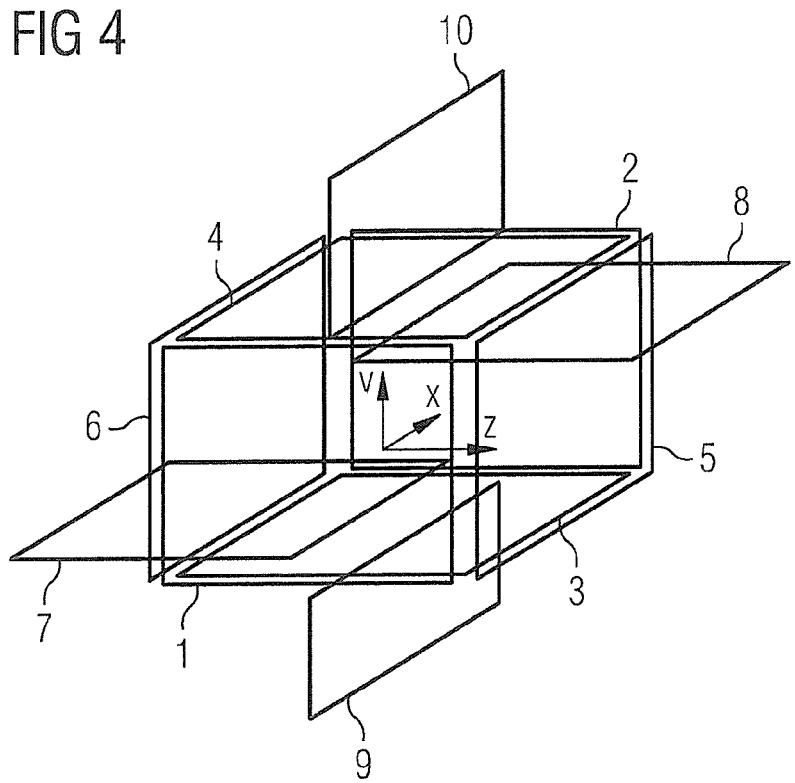

FIG. 3 and FIG. 4 respectively show two exemplary embodiments of coil systems to generate magnetic fields for the navigation requirements according to the above case (B). The shown examples essentially correspond to embodiments which are described in the aforementioned earlier German Patent Application Nr. 10 2008 004 871.2-35. The shown coil systems now have only ten coils because the coils 11 and 12 shown in the embodiments of FIG. 1 and FIG. 2 are no longer required since these coils serve for the generation of the field gradient $\partial B_z/\partial x$, which—according to case (B)—does not need to be controlled. The geometric arrangement of the coils of FIG. 3 thus corresponds to the arrangement according to FIG. 1, wherein the coils 9 and 10 have however been omitted. The association of the power amplifier with the coils can also take place according to the two variants described with reference to FIG. 1, wherein only the power amplifier with Nr. 8 for activation of the coil pair composed of coils 11 and 12 is omitted.

FIG. 4 shows a modification of the coil system of FIG. 3 which likewise is ascribed to the aforementioned earlier German Patent Application. The single difference of this embodiment relative to the embodiment of FIG. 3 is that now the coils 7 and 8 are arranged differently. These coils now are situated in the x-z plane and are arranged on opposite sides of the work space along the x-axis. With this coil arrangement the same effect is achieved as with the arrangement of the coils 7 and 8 in FIG. 3, meaning that these coils also serve to adjust the magnetic field component $\partial B_x/\partial y$. The activation of the individual coils of FIG. 4 can take place analogously based on the associations of power amplifiers with coils, as is described with reference to FIG. 2.

Figure 5:
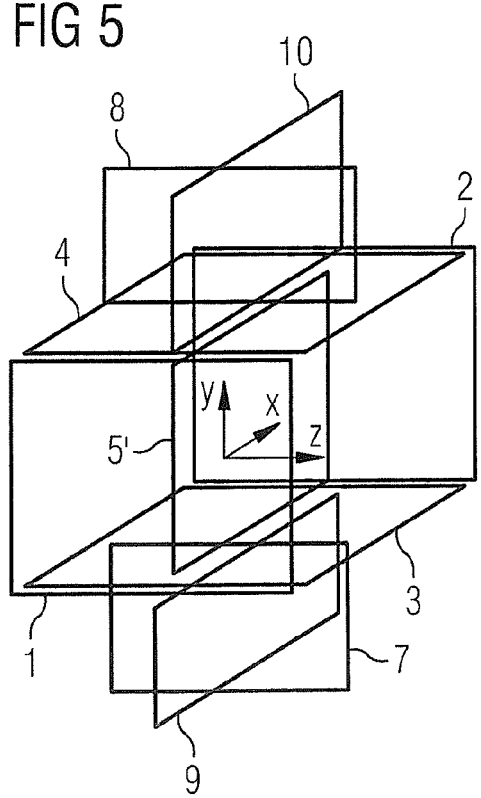
FIG. 5 schematically illustrates a nine coil system with seven power amplifiers according to a second embodiment of the present invention.

FIG. 5 shows a second embodiment of a coil system according to the invention with which a navigation of the endoscopy capsule based on the case (B) is enabled analogously to the embodiments of FIG. 3 and FIG. 4. The embodiment according to FIG. 5 is based on the realization that any coil pair among the coil pairs composed of coils 1, 2 and coils 3, 4 and the coils 5, 6 that are activated by a single power amplifier can be replaced by a single coil. In FIG. 5 the variant is shown in which the coils 5 and 6 of the embodiment of FIG. 3 are replaced by a single coil 5'. The remaining coils are arranged just as shown in the embodiment of FIG. 3. However, the coil system now has only nine coils, and for the embodiment of FIG. 5 seven power amplifiers are used which are associated with the coils as follows:

Power amplifier 1: Coil 1
Power amplifier 2: Coil 2
Power amplifier 3: Coil 3
Power amplifier 4: Coil 4
Power amplifier 5: Coil 5'
Power amplifier 6: Coils 9 and 10
Power amplifier 7: Coils 7 and 8

In a modification of the embodiment of FIG. 5, either the coil pair composed of coils 1 and 2 or the coil pair composed of coils 3 and 4 can also be replaced by a single coil, wherein in this case the coil pair composed of coils 5 and 6 remains along the y-axis. In an analogy to the embodiment of FIG. 5, all coils that correspond to the aforementioned first individual coils are activated by a single power amplifier, in contrast to which the coils 7, 8 and 9, 10 are respectively activated by a common power amplifier.

Figure 6:
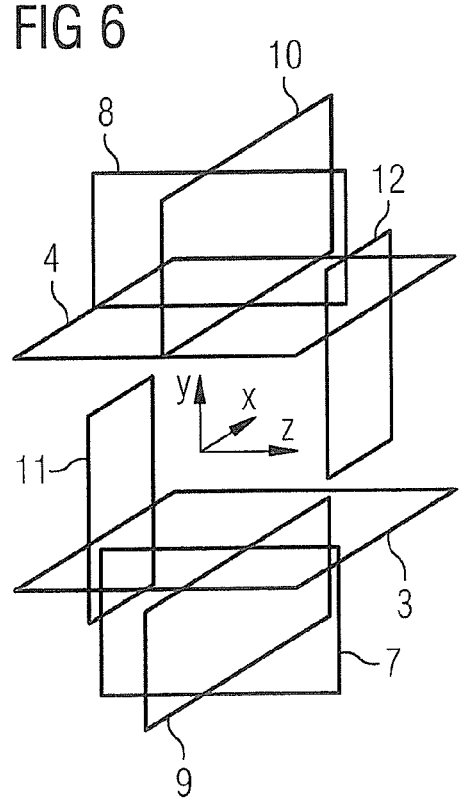
FIGS. 6 and 7 schematically illustrate an eight coil system with six power amplifiers and with seven power amplifiers, respectively, according to a third embodiment of the present invention.
Figure 7:
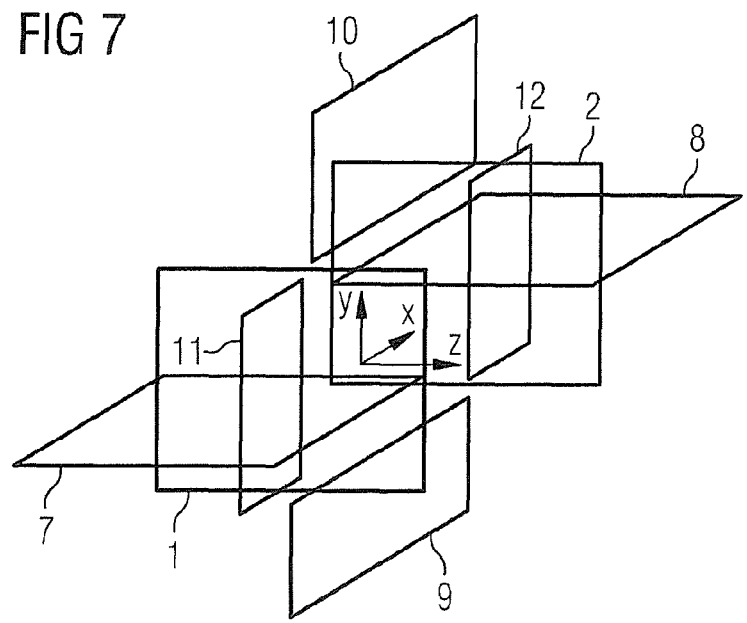

FIG. 6 and FIG. 7 pertain to embodiments according to the invention according to which a magnetic object should be capable of being arbitrarily aligned in space, wherein it is possible to exert magnetic forces only in the direction of the longitudinal axis of the capsule, and wherein the magnetic moment of the permanent magnet in the capsule is aligned perpendicular to the longitudinal axis of the capsule. This navigation requirement, which is subsequently designated as case (C), is in particular used for "tube navigation" of endoscopy capsules in the small intestine or, respectively, large intestine. Due to the alignment of the magnetic moment perpendicular to the capsule longitudinal axis, a rotation of the capsule around its longitudinal axis can thereby be generated, whereby—given helical capsules—a good forward movement of the capsule through the intestine is enabled by means of a corresponding rotation movement. In particular, the subsequent coil configuration according to the embodiments of FIGS. 6 and 7 can be used for helical capsules, which are disclosed in the publications US 2003/0020810 A1 or, respectively, US 2003/0181788 A1.

For the case (C.X) of a dipole moment $m_x$ aligned in the x-direction, the generated force must lie in the y-z plane. This means that no force component $F_x$ occurs and only entries in the columns with the numbers 2 and 3 of the matrix $U_2$ are relevant, which entries are multiplied with corresponding field gradients $\partial B_y/\partial x$ and $\partial B_z/\partial x$. For the case of a dipole moment $m_y$ aligned in the y-direction, which dipole moment corresponds with (C.Y), the force must lie in the x-z plane. No force component $F_y$ can then occur, such that only entries in the columns 2 and 4 from the matrix $U_2$ are relevant. For the case (C.Z) in which the magnetic dipole moment is directed in the z-direction, the force must lie in the x-y plane. This means that no $F_z$ force component occurs and only the columns 3 and 4 of the matrix $U_2$ are relevant. Overall only three gradients are thus required for the case (C), namely $\partial B_y/\partial x$, $\partial B_z/\partial x$ and $\partial B_z/\partial y$. In connection with the three basic magnetic field components, at least six power amplifiers are required in this case.

FIG. 6 shows an embodiment of a coil arrangement according to the invention to satisfy the navigation requirements according to case (C). The design of the embodiment of FIG. 6 resembles the design of the embodiment according to FIG. 1, wherein now however the coils 1, 2 and 5, 6 have been omitted. To generate the three field gradients $\partial B_y/\partial x$, $\partial B_z/\partial x$ and $\partial B_z/\partial y$ as well as the three basic magnetic field components, a feed with six or seven power amplifiers can take place. In the event that seven power amplifiers are used, corresponding power amplifiers with the numbers 1 through 7 are associated with the coils as follows:

Power amplifier 1: Coil 9
Power amplifier 2: Coil 10
Power amplifier 3: Coil 7
Power amplifier 4: Coil 8
Power amplifier 5: Coil 11
Power amplifier 6: Coil 12
Power amplifier 7: Coils 3 and 4

In one variant in which only six power amplifiers are used to activate the 8-coil system according to FIG. 6, the association between the power amplifiers and the coils takes place as follows:

Power amplifier 1: Coil 9
Power amplifier 2: Coil 10
Power amplifier 3: Coil 7
Power amplifier 4: Coil 8
Power amplifier 5: Coils 11 and 12
Power amplifier 6: Coils 3 and 4

FIG. 7 shows a further variant of an 8-coil system to satisfy the navigation requirements according to the above case (C).

The embodiment according to FIG. 7 differs from the embodiment according to FIG. 6 to the effect that the coils 7 and 8 that are used to generate the magnetic field component $\partial B_y/\partial x$ are now arranged along the x-axis in the x-z plane. Furthermore, instead of the coil pair 3, 4 the coil pair 1, 2 is used which is arranged in parallel planes on opposite sides of the work space along the x-axis.

Six or seven power amplifiers can again be used to activate the coils. In the variant with seven power amplifiers, these power amplifiers are associated with the coils as follows:

Power amplifier 1: Coil 9
Power amplifier 2: Coil 10
Power amplifier 3: Coil 7
Power amplifier 4: Coil 8
Power amplifier 5: Coil 11
Power amplifier 6: Coil 12
Power amplifier 7: Coils 1 and 2

In one variant in which only six power amplifiers are used to activate the coils, the power amplifiers with the numbers 1 through 6 are associated with the coils as follows:

Power amplifier 1: Coil 9
Power amplifier 2: Coil 10
Power amplifier 3: Coil 7
Power amplifier 4: Coil 8
Power amplifier 5: Coils 11 and 12
Power amplifier 6: Coils 1 and 2

According to a further navigation requirement, which is designated in the following as case (D), a magnetic capsule should be capable of being arbitrarily aligned in space, and it should be possible to exert magnetic fields on the capsule only in the direction of the longitudinal axis of the capsule, wherein the magnetic moment of the capsule is now aligned along the capsule longitudinal axis. This case (D) also advantageously pertains to the variant of the magnetic guidance of an endoscopy capsule for tube navigation in the small intestine and/or large intestine. However, in the variant (D) the capsule cannot be rotated around its longitudinal axis due to the magnetic dipole moment directed parallel to the longitudinal axis.

For the case (D.X) of a dipole moment $m_x$ aligned in the x-direction, only the force component $F_x$ is generated, meaning that only the column 1 of the matrix $U_2$ which is combined with the field gradient $\partial B_x/\partial x$ is relevant. For the case of a dipole moment $m_y$—case (D.Y)—directed in the y-direction, the force is aligned in the y-direction, meaning that only the force component $F_y$ occurs. In this case only the column 5 of the matrix $U_2$ which is combined with the field gradient $\partial B_y/\partial y$ is relevant. For the case of a dipole moment $m_z$—case (D.Z)—aligned in the z-direction, the force contains only the component $F_z$, meaning that only the columns 1 and 5 of the matrix $U_2$ which are combined with the corresponding field gradients $\partial B_x/\partial x$ or, respectively, $\partial B_y/\partial y$ are relevant. According to case (D), in addition to the three basic field components only two additional diagonal elements of the gradient matrix G must thus be generated because—due to the lack of spurs of the gradient matrix—so that: $\partial B_z/\partial z = -\partial B_x/\partial x - \partial B_y/\partial y$. Five power amplifiers are thus required to realize the case (D).

Figure 8:
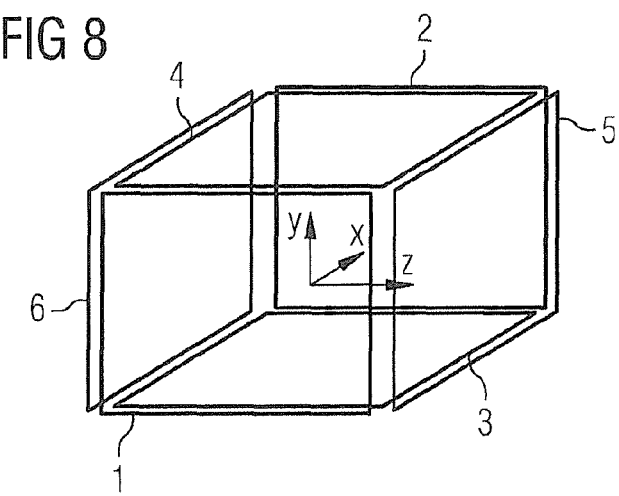
FIGS. 8 and 9 schematically illustrate a six coil system and a five coil system, respectively, with five power amplifiers according to a fourth embodiment of the present invention.
Figure 9:
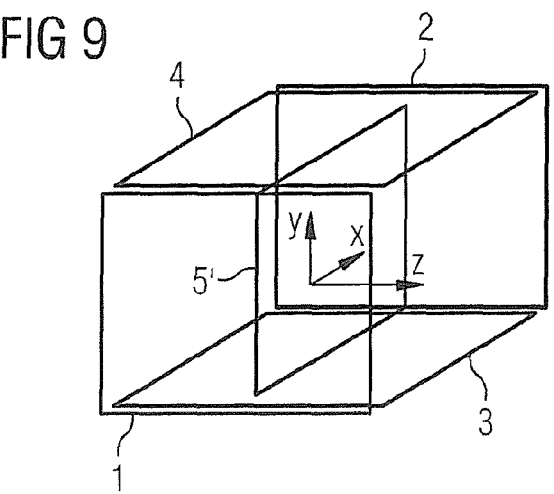

FIG. 8 and FIG. 9 show corresponding variants of coil systems to satisfy the navigation requirement according to case (D). According to the variant according to FIG. 8, the six individual coils 1 through 6 are used which (in the terminology of the Claims) correspond to the first individual coils. Since only five power amplifiers are required, one of the coil pairs composed of coils 1 and 2 and coils 3 and 4 and coils 5 and 6 can be activated by a common power amplifier. The following associations of power amplifiers with numbers 1 through 5 with the corresponding coils are consequently possible:

Variant a):
Power amplifier 1: Coils 1 and 2
Power amplifier 2: Coil 3
Power amplifier 3: Coil 4
Power amplifier 4: Coil 5
Power amplifier 5: Coil 6

Variant b):
Power amplifier 1: Coil 1
Power amplifier 2: Coil 2
Power amplifier 3: Coils 3 and 4
Power amplifier 4: Coil 5
Power amplifier 5: Coil 6

Variant c):
Power amplifier 1: Coil 1
Power amplifier 2: Coil 2
Power amplifier 3: Coil 3
Power amplifier 4: Coil 4
Power amplifier 5: Coils 5 and 6

FIG. 9 shows an additional embodiment to satisfy the navigation requirement according to case (D). That coil pair which is activated by a common power amplifier in the embodiment of FIG. 8 is now replaced by a single coil. FIG. 9 thereby shows the variant in which the coil pair made up of coils 5 and 6 is replaced with an individual coil 5'. It is likewise also possible to replace the coil pair composed of coils 1 and 2 or the coil pair composed of coils 3 and 4 with a single coil respectively arranged centrally between the coil pairs to be omitted. In the embodiment of FIG. 9, all coils are individually fed via a separate power amplifier. This means that the following association exists between power amplifiers with the numbers 1 through 5 and the coils:
Power amplifier 1: Coil 1
Power amplifier 2: Coil 2
Power amplifier 3: Coil 3
Power amplifier 4: Coil 4
Power amplifier 5: Coil 5'

Figure 10:
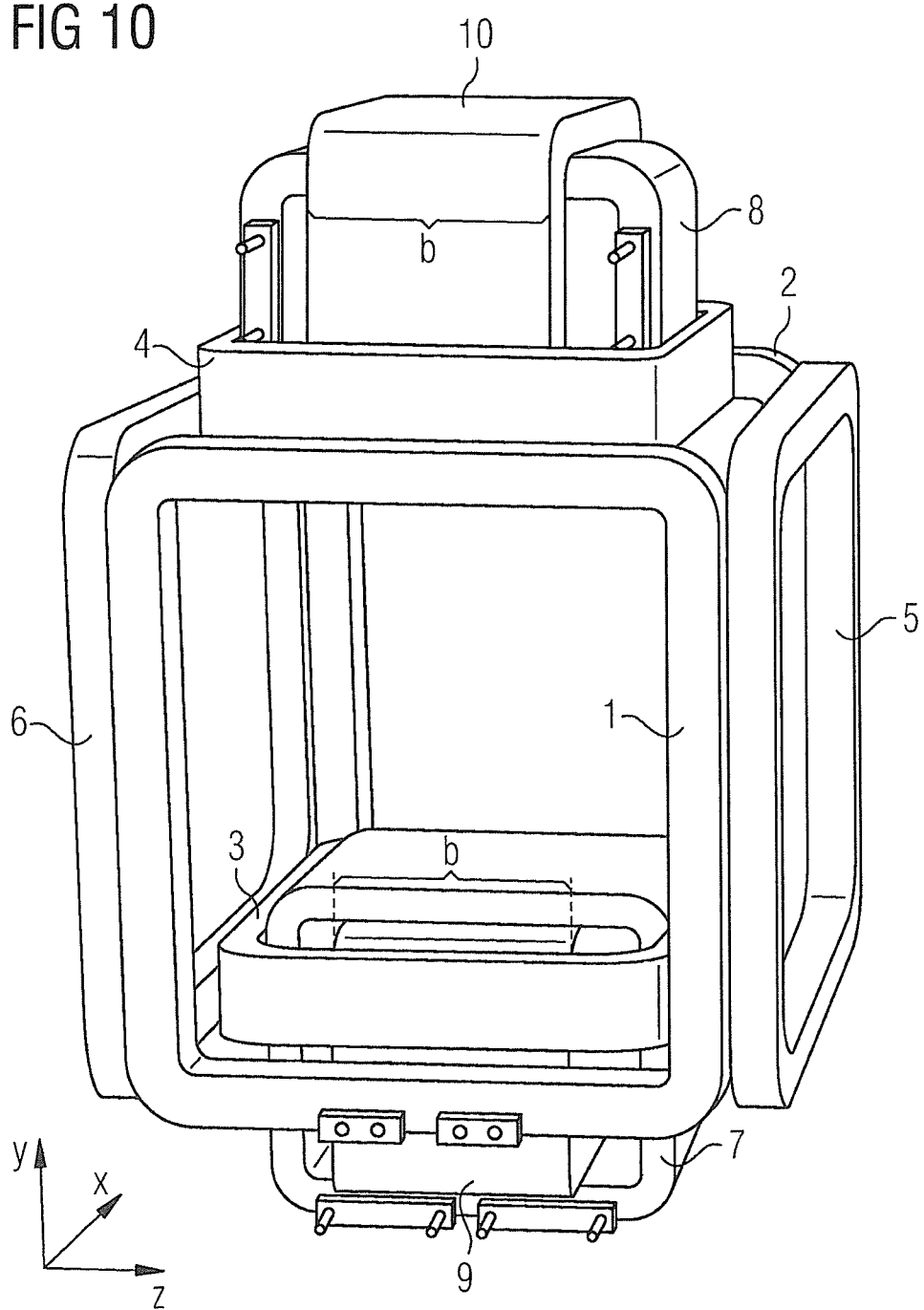
FIG. 10 is perspective view of an exemplary embodiment of a coil system according to FIG. 3.

FIG. 10 shows a concrete exemplary embodiment of a coil arrangement according to FIG. 3 in a perspective view, wherein the coils used in FIG. 10 can be used in all preceding embodiments according to FIG. 1 through FIG. 9. It is apparent that the individual coils 1 through 10 are fashioned as surface coils in this exemplary embodiment, wherein in addition to the coils 7 and 8 in particular the coils 9 and 10 are fashioned as broad surface coils whose respective width b is markedly greater than the thickness or winding height of the coils. Wide surface coils are advantageously also used in those embodiments in which a coil pair is replaced with a single, centrally arranged coil. At least this centrally arranged coil (which is designated with the reference character 5' in the preceding exemplary embodiments) is thereby fashioned as a wide surface coil.

Figure 11:
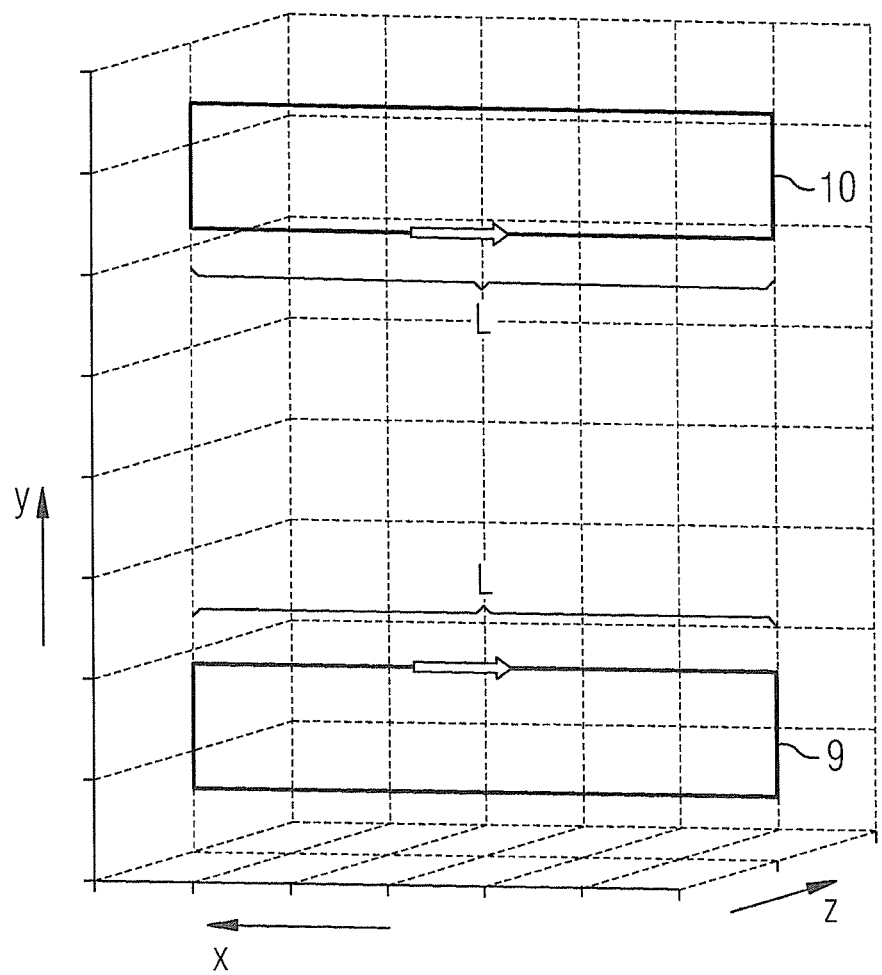
FIG. 11 schematically illustrates current flow through a coil pair in the coil arrangement according to FIG. 10.

FIG. 11 shows a corresponding current flow through the coils 9 and 10 shown in FIG. 10. The field gradient of the corresponding secondary diagonal element of the gradient matrix is thereby produced only by the primary conductor (which is indicated with the reference character L in FIG. 11). The remainder of the conductor in the coil—i.e. the return conductor—should be arranged optimally far removed from the work space. The current-carrying portion of the coil should also optimally be arranged as close as possible to the work space, from which the preferred embodiment of the coil 9 or, respectively, 10 as a broad surface coil results.

Based on the variants of the invention that are described above, minimal coil system configurations are achieved which can be realized at low cost—i.e. with an optimally low number of power amplifiers or, respectively, coils—corresponding to the requirements for the degrees of freedom of the movement of a magnetic object, in particular an endoscopy capsule equipped with a permanent magnet. In particular, the invention is based on the realization that the number of power amplifiers for activation of the coils or the number of coils can be reduced given corresponding navigation requirements.

Although modifications and changes may be suggested by those skilled in the art, it is the intention of the inventor to embody within the patent warranted heron all changes and modifications as reasonably and properly come within the scope of his contribution to the art.

The invention claimed is:

1. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
   exactly eleven individual coils that are:
      two first coil pairs, wherein one of the first coil pairs is associated with the first axis and the other of the first coil pairs is associated with the third axis;
      a single first individual coil that is associated with the second axis;
      a second coil pair that is associated with the first axis and is arranged in a plane that is spanned by the first and third axes; and
      two second coil pairs that are associated with the third axis and that are arranged essentially perpendicular to one another in planes, wherein one of the planes is spanned by the first and third axes and the other of the planes is spanned by the second and third axes; and
   at least one activation unit that controls current feed to the individual coils.

2. Coil arrangement according to claim 1, wherein at least two of said eleven individual coils are all activated by a common activation unit.

3. Coil arrangement according to claim 1 comprising exactly eight activation units, wherein:
   all first individual coils are respectively activated by separate activation units;
   the second coil pairs are respectively be activated by a common activation unit.

4. Coil arrangement according to claim 1, comprising a patient table configured to receive the patient to be examined thereon during operation of the coil arrangement, the patient table being configured to cause a longitudinal axis of a patient on the patient table to extend essentially in the direction of the second axis.

5. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
   exactly eleven individual coils that are:
      two first coil pairs, wherein one of the first coil pairs is associated with the first axis and the other of the first coil pairs is associated with the third axis;
      a single first individual coil that is associated with the second axis;
      a second coil pair that is associated with the first axis and is arranged in a plane that is spanned by the first and third axes;
      a second coil pair that is associated with the first axis and is arranged in a plane that is spanned by the first and second axes; and
      a second coil pair that is associated with the third axis and is arranged in a plane that is spanned by the first and third axes; and
   at least one activation unit that controls current feed to the individual coils.

6. Coil arrangement according to claim 5 comprising exactly eight activation units, wherein:
   all first individual coils are respectively activated by separate activation units;
   the second coil pairs are respectively be activated by a common activation unit.

7. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
   exactly nine individual coils, that are:
      two first coil pairs, wherein one of the first coil pairs is associated with the first axis and the other of the first coil pairs is associated with the third axis;
      a single first individual coil that is associated with the second axis; and
      two second coil pairs that are associated with the third axis that are arranged in planes essentially perpendicular to one another, wherein one of the planes is spanned by the first and third axes and the other of the planes is spanned by the second and third axes; and
   at least one activation unit that controls current feed to the individual coils.

8. Coil arrangement according to claim 7 comprising exactly seven activation units, wherein:
- all first individual coils are respectively activated by separate activation units; and
- the second coil pairs are respectively be activated by a common activation unit.

9. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
- exactly nine individual coils, that are:
  - two first coil pairs, wherein one of the first coil pairs is associated with the first axis and the other of the first coil pairs is associated with the third axis;
  - a single first individual coil that is associated with the second axis;
  - a second coil pair that is associated with the first axis and arranged in a plane that is spanned by the first and second axes; and
  - a second coil pair that is associated with the third axis and is arranged in a plane that is spanned by the first and third axes; and
- at least one activation unit that controls current feed to the individual coils.

10. Coil arrangement according to claim 9 comprising exactly seven activation units, wherein:
- all first individual coils are respectively activated by separate activation units; and
- the second coil pairs are respectively be activated by a common activation unit.

11. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
- exactly eight individual coils that are:
  - a first coil pair that is associated with the third axis;
  - a second coil pair that is associated with the first axis and is arranged in a plane that is spanned by the first and third axes;
  - two second coil pairs that are associated with the third axis and that are arranged essentially perpendicularly to one another in respective planes, wherein one of the respective planes is spanned by the first and third axes and the other of the respective planes is spanned by the second and third axes; and
- at least one activation unit that controls current feed to the individual coils.

12. Coil arrangement according to claim 11 comprising exactly seven activation units, wherein all second individual coils are respectively activated by separate activation units and the two first individual coils of the first coil pair are activated by a common activation unit.

13. Coil arrangement according to claim 11 comprising exactly six activation units, wherein
- the second individual coils of the second coil pair, which is associated with the first axis and is arranged in a plane that is spanned by the first and third axes is activated by a common activation unit;
- the two first individual coils of the first coil pair are activated by a common activation unit; and
- all remaining individual coils are activated by separate activation units.

14. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
- exactly eight individual coils, that are:
  - a first coil pair that is associated with the first axis;
  - a second coil pair that is associated with the first axis and is arranged in a plane that is spanned by the first and third axes;
  - a second coil pair that is associated with the first axis and is arranged in a plane that is spanned by the first and second axes; and
  - a second coil pair that is associated with the third axis and arranged in a plane that is spanned by the first and third axes; and
- exactly seven activation units, wherein all second individual coils are respectively activated by separate activation units and the two first individual coils of the first coil pair are activated by a common activation unit.

15. Coil arrangement for contact-free guidance of a magnetic object having a magnetic dipole moment in a workspace in a Cartesian coordinate system with three axes comprising a horizontal first axis, a horizontal second axis, and a vertical third axis, said coil arrangement comprising:
- exactly eight individual coils, that are:
  - a first coil pair that is associated with the first axis;
  - a second coil pair that is associated with the first axis and is arranged in a plane that is spanned by the first and third axes;
  - a second coil pair that is associated with the first axis and is arranged in a plane that is spanned by the first and second axes; and
  - a second coil pair that is associated with the third axis and arranged in a plane that is spanned by the first and third axes; and
- exactly six activation units, wherein:
  - the second individual coils of the second coil pair, which is associated with the first axis and is arranged in a plane that is spanned by the first and third axes is activated by a common activation unit;
  - the two first individual coils of the first coil pair are activated by a common activation unit; and
  - all remaining individual coils are activated by separate activation units.

16. Coil arrangement according to claim 1, wherein the activation units are power amplifiers.

17. Coil arrangement according to claim 1, wherein the individual coils are ring coils or saddle coils.

18. Coil arrangement according to claim 1, wherein at least some of the individual coils are surface coils, each having a width in the longitudinal direction that is greater than a thickness of the coil.

19. Coil arrangement according to claim 18 wherein said width is at least five times said thickness.

20. Coil arrangement for contact-free guidance of a magnetic object having a magnetic dipole moment in a workspace in a Cartesian coordinate system with three axes comprising a horizontal first axis, a horizontal second axis and a vertical third axis, said coil arrangement comprising:
- a plurality of individual coils that generate components of a magnetic field and components of magnetic gradient fields;
- the plurality of individual coils consisting of a plurality of first individual coils, wherein the workspace as seen from a direction of a longitudinal axis of each first individual coil, lies within a circumference of the respective first individual coil;
- at least one first coil pair consisting of two first individual coils respectively associated with at least one of the axes, the individual coils of said at least one first coil pair being arranged along the respective axis on opposite sides of the workspace in essentially parallel planes;

the first individual coils of said at least one first coil pair are activated by a common activation unit; and exactly five activation units, wherein the two first individual coils of the first coil pair are activated by a common activation unit and all remaining first individual coils are activated respectively by separate activation units.

21. Coil arrangement according to claim 20 comprising exactly six first individual coils, with a first coil pair associated with each axis.

22. Coil arrangement according to claim 20, wherein the activation units are power amplifiers.

23. Coil arrangement according to claim 20, wherein the individual coils are ring coils or saddle coils.

24. Coil arrangement according to claim 20, wherein at least some of the individual coils are surface coils, each having a width in the longitudinal direction that is greater than a thickness of the coil.

25. Coil arrangement according to claim 24 wherein said width is at least five times said thickness.

26. Coil arrangement according to claim 20, comprising a patient table configured to receive the patient to be examined thereon during operation of the coil arrangement, the patient table being configured to cause a longitudinal axis of a patient on the patient table to extend essentially in the direction of the second axis.

27. Coil arrangement for contact-free guidance of a magnetic object having a magnetic dipole moment in a workspace in a Cartesian coordinate system with three axes comprising a horizontal first axis, a horizontal second axis and a vertical third axis, said coil arrangement comprising:

a plurality of individual coils that generate components of a magnetic field and of magnetic gradient fields;

at least one activation unit that controls current feed to the individual coils;

the plurality of individual coils consisting of exactly five first individual coils, wherein the work space, as seen from a direction of a longitudinal axis of each first individual coil, lying within a circumference of each first individual coil;

at least one first coil pair, consisting of two of said first individual coils, being associated with at least one of the axes, the first individual coils of said at least one first coil pair being arranged along the respective axis on opposite sides of the work space in essentially parallel planes; and a single first individual coil associated with at least one other of the axes, wherein the work space is surrounded at least partially be a circumference of said single first individual coil.

28. Coil arrangement according to claim 27, wherein all first individual coils are respectively activated by separate activation units.

29. Coil arrangement according to claim 27, wherein the activation units are power amplifiers.

30. Coil arrangement according to claim 27, wherein the individual coils are ring coils or saddle coils.

31. Coil arrangement according to claim 27, wherein at least some of the individual coils are surface coils, each having a width in the longitudinal direction that is greater than a thickness of the coil.

32. Coil arrangement according to claim 31 wherein said width is at least five times said thickness.

33. Coil arrangement according to claim 27, comprising a patient table configured to receive the patient to be examined thereon during operation of the coil arrangement, the patient table being configured to cause a longitudinal axis of a patient on the patient table to extend essentially in the direction of the second axis.

* * * * *